United States Patent
Jiang et al.

(10) Patent No.: US 9,586,912 B2
(45) Date of Patent: Mar. 7, 2017

(54) 2-SUBSTITUTED-2H-1, 2, 3-TRIAZOLE DERIVATIVE AND ITS PREPARATION METHOD

(75) Inventors: Yueheng Jiang, Jiangsu (CN); Limin Que, Jiangsu (CN); Tong Cai, Jiangsu (CN); Dongguang Qin, Jiangsu (CN)

(73) Assignee: ABA Chemicals Corporation, Jiangshu (CN)

( * ) Notice: Subject to any disclaimer, the term of this patent is extended or adjusted under 35 U.S.C. 154(b) by 0 days.

(21) Appl. No.: 14/422,646

(22) PCT Filed: Aug. 24, 2012

(86) PCT No.: PCT/CN2012/001145
§ 371 (c)(1),
(2), (4) Date: Feb. 19, 2015

(87) PCT Pub. No.: WO2014/029042
PCT Pub. Date: Feb. 27, 2014

(65) Prior Publication Data
US 2015/0232431 A1    Aug. 20, 2015

(51) Int. Cl.
*C07D 249/04* (2006.01)
*C07D 405/04* (2006.01)
*C07D 405/06* (2006.01)

(52) U.S. Cl.
CPC ......... *C07D 249/04* (2013.01); *C07D 405/04* (2013.01); *C07D 405/06* (2013.01)

(58) Field of Classification Search
None
See application file for complete search history.

(56) References Cited

PUBLICATIONS

SYNLETT Accounts and Rapid Communications in Synthetic Organic Chemistry; Regioselective Synthesis of Polysubstituted N2-Alkyl/Aryl-1,2,3-Triazoles via 4-Bromo-5-iodo-1,2,3-triazole; May 4, 2006; pp. 1052-1056.
STN Intenatonal on the Web; www.cas.org/training/stn/database-specific;5-chloro-2-(phenylmenthy1)-2H-1,2,3-Triazone-4 carboxylic acid; molecular formula is C10H8C1N302, 1 page.

*Primary Examiner* — Alicia L Otton
(74) *Attorney, Agent, or Firm* — LeClairRyan

(57) ABSTRACT

Disclosed is a 2-substituted-2H-1,2,3-triazole derivative, a compound as represented by formula I or II. Also disclosed is a preparation method of the compound as represented by formula I or II, in particular to a preparation method of 2-substituted-4-bromo-5-chloro-1H-1,2,3-triazole, 2-substituted-4-bromo-5-iodo-1H-1,2,3-triazole, and 2-substituted-5-chloro-1H-1,2,3-triazole-4-carboxylic acid. The preparation methods of the present invention are simple and feasible, and has high yield of the obtained compounds.

6 Claims, No Drawings

2-SUBSTITUTED-2H-1, 2, 3-TRIAZOLE DERIVATIVE AND ITS PREPARATION METHOD

FIELD OF THE INVENTION

The present invention relates to the filed of organic synthetic intermediate preparative technology, and in particular, to a 2-substituted-2H-1,2,3-triazole derivative and its preparation method.

BACKGROUND OF THE INVENTION

The 2-substituted-2H-1,2,3-triazole derivative is a new type of compound having huge development value. A compound with triazole as mother nucleus has extensive potential application value, which is an important intermediate of compounds such as many drugs, herbicide and insecticide etc available at present, which is also a primary pharmacophore in a great many drug molecules.

SUMMARY OF THE INVENTION

The object of the present invention is to provide a new type of 2-substituted-2H-1,2,3-triazole derivative and its preparation method.

In order to achieve the aforementioned inventive object, the present invention adopts the technical solutions as follows:

The present invention provides a 2-substituted-2H-1,2,3-triazole derivative, the 2-substituted-2H-1,2,3-triazole derivative has the following structure:

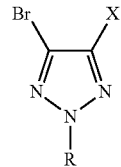

Formula I wherein R represents alkyl, aryl, aralkyl, cycloalkyl, cycloalkyl alkyl, heteroaryl, heteroaryl alkyl, heterocyclic alkyl; X represents chlorine, iodine.

Wherein when X in the formula 1 is chlorine, the 2-substituted-2H-1,2,3-triazole derivative is 2-substituted-4-bromo-5-chloro-1H-1,2,3-triazole shown in the following formula IV

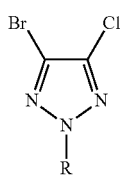

Formula IV wherein R represents alkyl, aryl, aralkyl, cycloalkyl, cycloalkyl alkyl, heteroaryl, heteroaryl alkyl, heterocyclic alkyl.

Wherein when X in the formula I is iodine, the 2-substituted-2H-1,2,3-triazole derivative is 2-substituted-4-bromo-5-iodo-1H-1,2,3-triazole shown in the following formula V

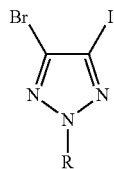

Formula V wherein R represents alkyl, aryl, aralkyl, cycloalkyl, cycloalkyl alkyl, heteroaryl, heteroaryl alkyl, heterocyclic alkyl.

A preparation method of the aforementioned 2-substituted-2H-1,2,3-triazole derivative, comprises the following steps:

dissolving the compound shown in the following formula III in mass to volume ratio of 1:2~20 of diethyl ether, tetrahydrofuran or 1,4-dioxane or methyltetrahydrofuran, cooling to −78~0° C., adding isopropylmagnesium chloride or isopropylmagnesium chloride-lithium chloride composite, stirring for 0.5~2 hours, inleting chlorine or adding N-chlorosuccinimide, 1,3-dichloro-5,5-dimethylhydantoin, or adding iodine, stirring for 5~30 minutes, heating up to room temperature, extracting by using organic solvent after quenching by using saturated ammonium chloride aqueous solution, drying via anhydrous sodium sulfate or anhydrous magnesium sulfate, concentrating to dry under reduced pressure, recrystallizing the obtained concentrate to obtain the 2-substituted-2H-1,2,3-triazole derivative;

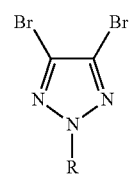

Formula III wherein R represents alkyl, aryl, aralkyl, cycloalkyl, cycloalkyl alkyl, heteroaryl, heteroaryl alkyl, heterocyclic alkyl.

Specifically, the molar ratio of the compound shown in formula III to isopropyl magnesium chloride or isopropylmagnesium chloride-lithium chloride composite is 1:0.8~1.5, the molar ratio of the compound shown in formula III to chlorine or N-chlorosuccinimide, 1,3-dichloro-5,5-dimethylhydantoin, iodine is 1:1~10, the organic solvent is one of or a mixture of two or more than two, in arbitrary proportion, of fatty acids esters or ethers, including one of or a mixture of two or more than two, in arbitrary proportion, of ethyl formate, propyl formate, butyl formate, methyl acetate, ethyl acetate, propyl acetate, butyl acetate, isopropyl acetate, isobutyl acetate, amyl acetate, isoamyl acetate, methyl propionate, ethyl propionate, propyl propionate, butyl propionate and amyl propionate, diethyl ether, propyl ether, isopropyl ether, methyl tertiary butyl ether.

The present invention also provides another kind of 2-substituted-2H-1,2,3-triazole derivative, the 2-substituted-2H-1,2,3-triazole derivative has the following structure:

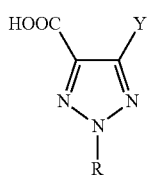

Formula II wherein R represents alkyl, aryl, aralkyl, cycloalkyl, cycloalkyl alkyl, heteroaryl, heteroaryl alkyl, heterocyclic alkyl; Y represents chlorine.

Preferably, the 2,4-disubstituted-2H-1,2,3-triazole derivative is 2-substituted-5-chloro-1H-1,2,3-triazole-4-carboxylic acid of formula VI

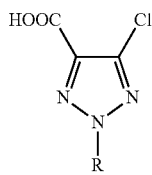

Formula VI wherein R represents alkyl, aryl, aralkyl, cycloalkyl, cycloalkyl alkyl, heteroaryl, heteroaryl alkyl, heterocyclic alkyl.

A preparation method of another kind of 2-substituted-2H-1,2,3-triazole derivative, comprises steps:

dissolving the compound shown in the following formula III in mass to volume ratio of 1:2~20 of diethyl ether, tetrahydrofuran or 1,4-dioxane or methyltetrahydrofuran, cooling to −78~0° C., adding isopropylmagnesium chloride or isopropylmagnesium chloride-lithium chloride composite, stirring for 0.5~2 hours, inleting chlorine or adding N-chlorosuccinimide, 1,3-dichloro-5,5-dimethylhydantoin, stirring for about 5~30 minutes, heating up to room temperature, extracting by using organic solvent after quenching by using saturated ammonium chloride aqueous solution, drying via anhydrous sodium sulfate or anhydrous magnesium sulfate, concentrating to dry under reduced pressure, recrystallizing the obtained concentrate to obtain 2-substituted-4-bromo-5-chloro-1H-1,2,3-triazole of formula IV

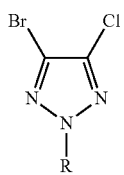

Formula IV wherein R represents alkyl, aryl, aralkyl, cycloalkyl, cycloalkyl alkyl, heteroaryl, heteroaryl alkyl, heterocyclic alkyl;

dissolving the compound shown in formula IV in mass to volume ratio 1:2~20 of diethyl ether, tetrahydrofuran, methyltetrahydrofuran or 1,4-dioxane, cooling to −20~30° C., adding isopropylmagnesium chloride-lithium chloride composite, stirring for 0.5~5 hours, cooling to −50~20° C., inleting carbon dioxide gas for about 10~30 minutes, heating up to room temperature, extracting by using organic solvent after adjusting pH=1~5 by using hydrochloric acid, drying via anhydrous sodium sulfate or anhydrous magnesium sulfate, concentrating to dry under reduced pressure, recrystallizing the obtained concentrate to obtain the 2-substituted-2H-1,2,3-triazole derivative.

Wherein the molar ratio of the compound of formula III to isopropyl magnesium chloride or isopropylmagnesium chloride-lithium chloride composite is 1:0.8~1.5, the molar ratio of the compound of formula III to carbon dioxide is 1:1~10, the organic solvent is one of or a mixture of two or more than two, in arbitrary proportion, of fatty acids esters or ethers, including one of or a mixture of two or more than two, in arbitrary proportion, of ethyl formate, propyl formate, butyl formate, methyl acetate, ethyl acetate, propyl acetate, butyl acetate, isopropyl acetate, isobutyl acetate, amyl acetate, isoamyl acetate, methyl propionate, ethyl propionate, propyl propionate, butyl propionate and amyl propionate, diethyl ether, propyl ether, isopropyl ether, methyl tertiary butyl ether.

The equations of the aforementioned preparation method of the 2-substituted-2H-1,2,3-triazole derivative provided by the present invention are shown as follows:

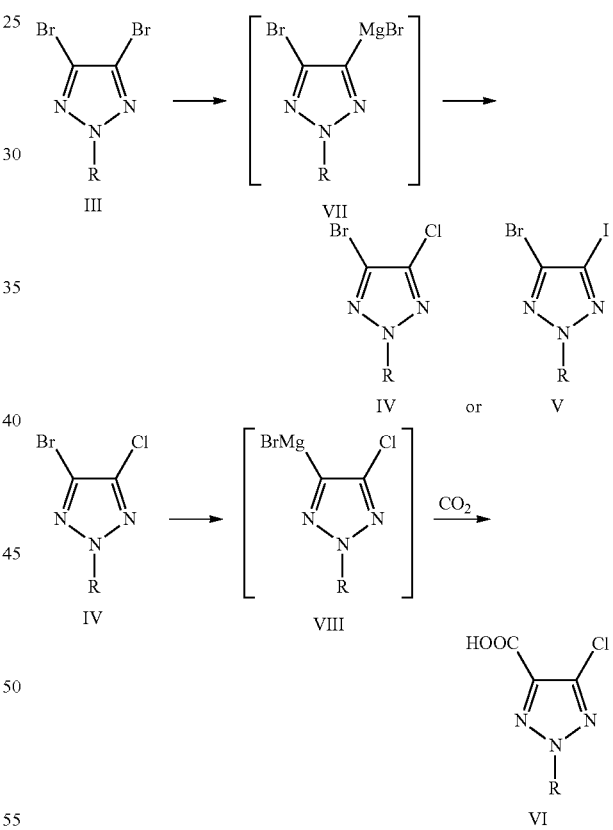

Isopropylmagnesium chloride or isopropylmagnesium chloride-lithium chloride composite of the present invention is different molar concentration of tetrahydrofuran solution, 2-methyl tetrahydrofuran solution or diethyl ether solution thereof, which commercially available concentration is usually 1.0~2.0 mole/litre.

The molar ratio of the compound shown in formula III or the compound shown in formula IV to isopropylmagnesium chloride or isopropylmagnesium chloride-lithium chloride composite is 1:08~1.5, preferably is 1:08~1.2.

The molar ratio of the compound shown in formula III to chlorine or N-chlorosuccinimide, 1,3-dichloro-5,5-dimethylhydantoin, iodine or carbon dioxide is 1:1~10, preferably is 1:2~5.

The method of the recrystallizing includes the following steps: adding the concentrate in solvent according to mass to volume ratio of 1:1~100, stirring for 0.5~24 hours at −20~50° C., filtering, vacuum drying, obtaining a pure product.

The solvent is one of or a mixture of two or more than two, in arbitrary proportion, of water, alcohols, fatty acids esters, ketones, ethers and hydrocarbons, including one of or a mixture of two or more than two, in arbitrary proportion, of methyl alcohol, ethyl alcohol, n-propyl alcohol, isopropanol, n-butyl alcohol, tert-butanol, ethyl formate, propyl formate, butyl formate, methyl acetate, ethyl acetate, propyl acetate, butyl acetate, isopropyl acetate, isobutyl acetate, amyl acetate, isoamyl acetate, methyl propionate, ethyl propionate, propyl propionate, butyl propionate and amyl propionate, acetone, 2-butanone, cyclopentanone and cyclohexanone, diethyl ether, propyl ether, isopropyl ether, methyl tertiary butyl ether and tetrahydrofuran, 1,4-dioxane, petroleum ether, n-hexane, cyclohexane, methylcyclohexane and n-heptane. Preferably is a mixed solvent of methyl tertiary butyl ether and n-hexane, or isopropanol and water in arbitrary proportion.

The preparation method of the 2,4-disubstituted-2H-1,2,3-triazole derivative of the present invention is simple and feasible while the yield of the obtained compound is high.

DETAILED DESCRIPTION OF THE EMBODIMENTS

The present invention will be further explained below in combination with specific examples.

EXAMPLE 1

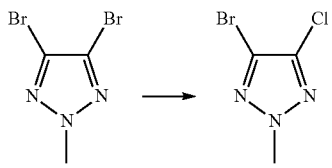

3.0 g (12.45 mmol) of 2-methyl-4,5-dibromo-2H-1,2,3-triazole was dissolved in 25 ml of tetrahydrofuran, cooled to −20~−10° C., 6.85 ml (13.7 mmol) of 2.0M isopropylmagnesium chloride tetrahydrofuran solution was added dropwise slowly over 30 minutes. Once the dropwise addition was completed, stirring was continued for 30~60 minutes. Chlorine was inleted slowly until reaction liquid was no longer heating up. Reaction liquid was added by 20 ml of saturated ammonium chloride aqueous solution, extracted using 30 ml of methyl tertiary butyl ether, dried by anhydrous sodium sulfate, and wasw concentrated to dry under reduced pressure. The residual solid was added by 20 ml of methyl tertiary butyl ether/n-hexane (⅕), heated to reflux for 1 hour, cooled to 0~10° C., continued to be stirred for 1 hour, filtered, vacuum dried under a temperature <40° C. 2.06 g of 2-methyl-4-bromo-5-chloro-2H-1,2,3-triazole solid was obtained, and the yield was 85%. $^1$H NMR (CDCl$_3$, 400 MHz): δ 4.15 (s, 3H); $^{13}$C NMR (CDCl$_3$, 400 MHz): δ 137.0, 120.8, 43.1.

EXAMPLE 2

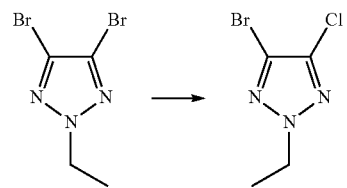

The operation method was the same as that of Example 1, 2-methyl-4,5-dibromo-2H-1,2,3-triazole was replaced with 3.17 g (12.45 mmol) of 2-ethyl-4,5-dibromo-2H-1,2,3-triazole. 2.33 g of 2-ethyl-4-bromo-5-chloro-2H-1,2,3-triazole solid was obtained, the yield was 89%. $^1$H NMR (CDCl$_3$, 400 MHz): δ 4.40 (q, J=7.2 Hz, 2H), 1.54 (t, J=7.2 Hz, 3H); $^{13}$C NMR (CDCl$_3$ 400 MHz): δ 136.7, 120.5, 51.7, 14.5.

EXAMPLE 3

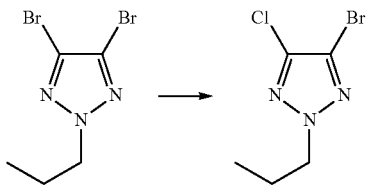

The operation method was the same as that of Example 1, 2-methyl-4,5-dibromo-2H-1,2,3-triazole was replaced with 3.35 g (12.45 mmol) of 2-n-propyl-4,5-dibromo-2H-1,2,3-triazole. 2.52 g of 2-n-propyl-4-bromo-5-chloro-2H-1,2,3-triazole oily matter was obtained, the yield was 90%. $^1$H NMR (CDCl$_3$, 400 MHz): δ 4.30 (t, J=7.2 Hz, 2H), 1.99-1.93 (m, 2H), 0.93 (t, J=7.2 Hz, 3H); $^{13}$C NMR (CDCl$_3$, 400 MHz): δ 136.7, 120.5, 58.2, 22.9, 10.9.

EXAMPLE 4

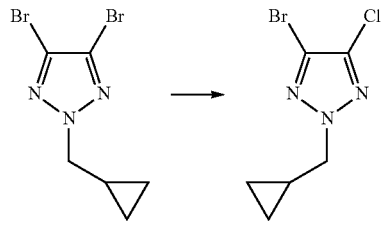 [SMILES: Brc1nn(CC2CC2)nc1Br ; Clc1nn(CC2CC2)nc1Br]

The operation method was the same as that of Example 1, 2-methyl-4,5-dibromo-2H-1,2,3-triazole was replaced with 3.50 g (12.45 mmol) of 2-cyclopropyl methyl-4,5-dibromo-2H-1,2,3-triazole. 2.71 g of 2-cyclopropyl methyl-4-bromo-5-chloro-2H-1,2,3-triazole oily matter was obtained, the yield was 92%. $^1$H NMR (CDCl$_3$, 400 MHz): δ 4.18 (d, J=7.6 Hz, 2H), 1.40-1.33 (m, 1H), 0.67 (m, 2H), 0.43 (m, 2H); $^{13}$C NMR (CDCl$_3$, 400 MHz): δ 136.8, 120.6, 61.3, 10.8, 4.0.

EXAMPLE 5

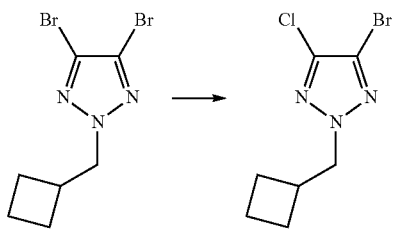 [SMILES: Brc1nn(CC2CCC2)nc1Br ; Clc1nn(CC2CCC2)nc1Br]

The operation method was the same as that of Example 1, 2-methyl-4,5-dibromo-2H-1,2,3-triazole was replaced with 3.67 g (12.45 mmol) of 2-cyclobutyl methyl-4,5-dibromo-2H-1,2,3-triazole. 2.84 g of 2-cyclobutyl methyl-4-bromo-5-chloro-2H-1,2,3-triazole oily matter was obtained, the yield was 91%. $^1$H NMR (CDCl$_3$, 400 MHz): δ 4.34 (d, J=7.2 Hz, 2H), 2.93-2.85 (m, 1H), 2.11-2.04 (m, 2H), 1.95-1.78 (m, 4H); $^{13}$C NMR (CDCl$_3$, 400 MHz): δ 136.7, 120.5, 61.2, 35.0, 25.6, 18.1.

EXAMPLE 6

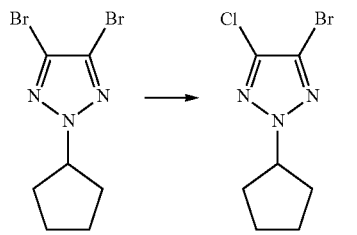 [SMILES: Brc1nn(C2CCCC2)nc1Br ; Clc1nn(C2CCCC2)nc1Br]

The operation method was the same as that of Example 1, 2-methyl-4,5-dibromo-2H-1,2,3-triazole was replaced with 3.67 g (12.45 mmol) of 2-cyclopentyl-4,5-dibromo-2H-1,2,3-triazole. 2.87 g of 2-cyclopentyl-4-bromo-5-chloro-2H-1,2,3-triazole oily matter was obtained, the yield was 92%. $^1$H NMR (CDCl$_3$, 500 MHz): δ 4.94-4.4.88 (m, 1H), 2.18-2.13 (m, 4H), 1.92-1.84 (m, 2H), 1.73-1.66 (m, 2H); $^{13}$C NMR (CDCl$_3$, 500 MHz) δ 136.3, 120.1, 67.9, 32.6, 24.2.

EXAMPLE 7

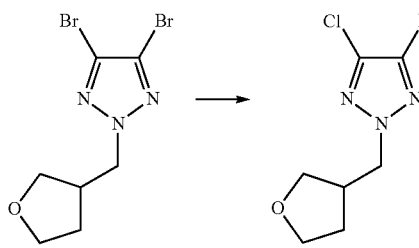

The operation method was the same as that of Example 1, 2-methyl-4,5-dibromo-2H-1,2,3-triazole was replaced with 3.87 g (12.45 mmol) of 2-(tetrahydrofuran-3-methyl)-4,5-dibromo-2H-1,2,3-triazole. 2.92 g of 2-(tetrahydrofuran-3-methyl)-4-bromo-5-chloro-2H-1,2,3-triazole oily matter was obtained, the yield was 88%. $^1$H NMR (CDCl$_3$, 400 MHz): δ 4.34 (d, J=7.6, 2H), 3.93-3.88 (m, 1H), 3.82-3.73 (m, 2H), 3.62 (dd, J=5.2, 9.2 Hz, 1H), 2.94-2.86 (m, 1H), 2.10-2.01 (m, 1H), 1.73-1.68 (m, 1H); $^{13}$C NMR (CDCl$_3$, 400 MHz): δ 137.2, 121.0, 70.6, 67.5, 58.7, 39.3, 29.6.

EXAMPLE 8

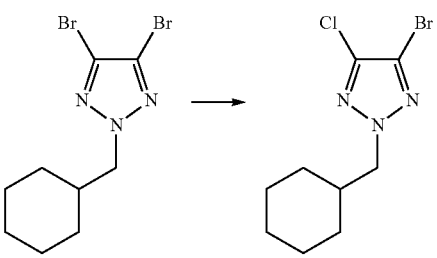 [SMILES: Brc1nn(CC2CCCCC2)nc1Br ; Clc1nn(CC2CCCCC2)nc1Br]

The operation method was the same as that of Example 1, 2-methyl-4,5-dibromo-2H-1,2,3-triazole was replaced with 4.0 g (12.45 mmol) of 2-cyclohexyl methyl-4,5-dibromo-2H-1,2,3-triazole. 2.95 g of 2-cyclohexyl methyl-4-bromo-5-chloro-2H-1,2,3-triazole oily matter was obtained, the yield was 85%. $^1$H NMR (CDCl$_3$, 400 MHz): δ 4.17 (d, J=7.6 Hz, 2H), 2.02-1.94 (m, 1H), 1.75-1.58 (m, 5H), 1.28-1.13 (m, 3H), 1.04-0.94 (m, 2H); $^{13}$C NMR (CDCl$_3$, 400 MHz): δ 136.7, 120.4, 62.6, 38.3, 30.3, 26.1, 25.5.

EXAMPLE 9

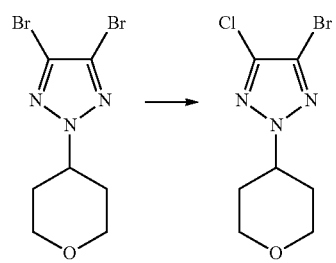 [SMILES: Brc1nn(C2CCOCC2)nc1Br ; Clc1nn(C2CCOCC2)nc1Br]

The operation method was the same as that of Example 1, 2-methyl-4,5-dibromo-2H-1,2,3-triazole was replaced with 3.87 g (12.45 mmol) of 2-(4-tetrahydropyran)-4,5-dibromo-2H-1,2,3-triazole. 2.95 g of 2-(4-tetrahydropyran)-4-bromo-5-chloro-2H-1,2,3-triazole solid was obtained, the yield was 89%. $^1$H NMR (CDCl$_3$, 400 MHz): δ 4.62-4.54 (m, 1H), 4.08 (dt, J=3.6, 11.6 Hz, 2H), 3.53 (dt, J=2.8, 11.6 Hz, 2H), 2.25-2.15 (m, 4H); $^{13}$C NMR (CDCl$_3$, 400 MHz): δ 136.9, 120.7, 66.2, 62.5, 32.0.

EXAMPLE 10

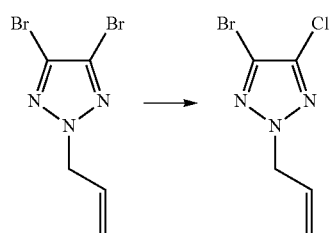

The operation method was the same as that of Example 1, 2-methyl-4,5-dibromo-2H-1,2,3-triazole was replaced with 3.32 g (12.45 mmol) of 2-allyl-4,5-dibromo-2H-1,2,3-triazole. 2.49 g of 2-allyl-4-bromo-5-chloro-2H-1,2,3-triazole oily matter was obtained, the yield was 90%. ¹H NMR (CDCl₃, 500 MHz): δ 6.07-5.99 (m, 1H), 5.35 (dd, J=0.5, 4.0 Hz, 1H), 5.25 (dd, J=0.5, 11.0 Hz, 1H), 4.95 (dt, J=1.0, 7.5 Hz, 2H); ¹³C NMR (CDCl₃, 500 MHz): δ 137.3, 130.3, 121.1, 120.8, 58.8.

EXAMPLE 11

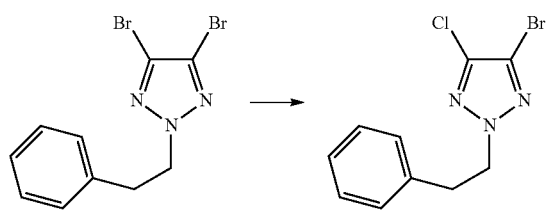 [SMILES: Brc1nn(CCc2ccccc2)nc1Br ; Clc1nn(CCc2ccccc2)nc1Br]

The operation method was the same as that of Example 1, 2-methyl-4,5-dibromo-2H-1,2,3-triazole was replaced with 4.12 g (12.45 mmol) of 2-phenethyl-4,5-dibromo-2H-1,2,3-triazole. 3.10 g of 2-phenethyl-4-bromo-5-chloro-2H-1,2,3-triazole oily matter was obtained, the yield was 87%. ¹H NMR (CDCl₃, 500 MHz): δ 7.30 (t, J=2.5 Hz, 2H), 7.26-7.23 (m, 1H), 7.16 (d, J=7.0 Hz, 2H), 4.56 (t, J=7.5 Hz, 2H), 3.21 (t, J=7.5 Hz, 2H); ¹³C NMR (CDCl₃, 500 MHz): δ 137.0, 136.6, 128.8, 128.7, 127.1, 120.7, 57.6, 35.8.

EXAMPLE 12

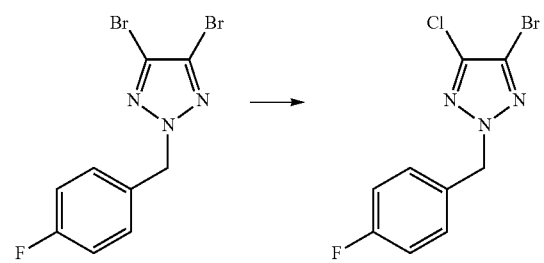 [SMILES: Fc1ccc(Cn2nc(Br)c(Br)n2)cc1 ; Fc1ccc(Cn2nc(Cl)c(Br)n2)cc1]

The operation method was the same as that of Example 1, 2-methyl-4,5-dibromo-2H-1,2,3-triazole was replaced with 4.17 g (12.45 mmol) of 2-p-fluorobenzyl-4,5-dibromo-2H-1,2,3-triazole. 2.89 g of 2-p-fluorobenzyl-4-bromo-5-chloro-2H-1,2,3-triazole solid was obtained, the yield was 80%. ¹H NMR (CDCl₃, 400 MHz): δ 7.35 (dd, J=8.4, 8.8 Hz, 2H), 7.05 (t, J=8.8 Hz, 2H), 5.44 (s, 2H); ¹³C NMR (CDCl₃, 400 MHz): δ 163.0 (d, J=247.0 Hz), 137.6, 130.4 (d, J=9.0 Hz), 129.6 (d, J=3.0 Hz), 121.5, 116.0 (d, J=22.0 Hz), 59.4.

EXAMPLE 13

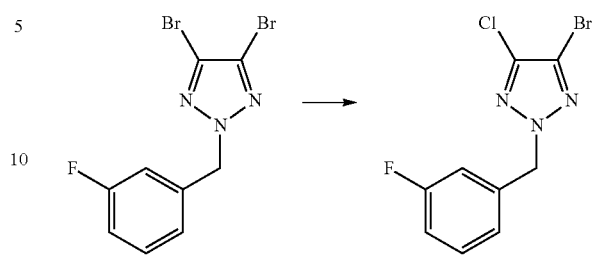

The operation method was the same as that of Example 1, 2-methyl-4,5-dibromo-2H-1,2,3-triazole was replaced with 4.17 g (12.45 mmol) of 2-m-fluorobenzyl-4,5-dibromo-2H-1,2,3-triazole. 2.97 g of 2-m-fluorobenzyl-4-bromo-5-chloro-2H-1,2,3-triazole solid was obtained, the yield was 82%. ¹H NMR (CDCl₃, 400 MHz): δ 7.36-7.31 (m, 1H), 7.12 (d, J=7.6 Hz, 1H), 7.06-7.03 (m, 2H), 5.47 (s, 2H); ¹³C NMR (CDCl₃, 400 MHz): δ 162.8 (d, J=246.0 Hz), 137.8, 136.0 (d, J=7.3 Hz), 130.6 (d, J=8.2 Hz), 124.0 (d, J=3.1 Hz), 121.6, 116.0 (d, J=20.9 Hz), 115.4 (d, J=23.0 Hz), 59.5 (d, J=20.0 Hz).

EXAMPLE 14

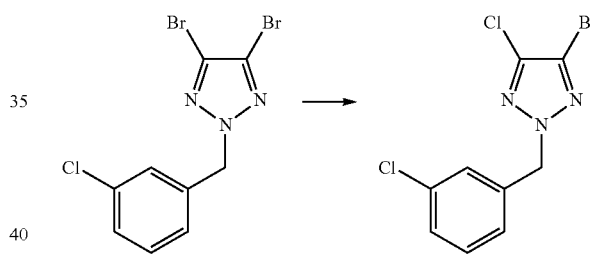

The operation method was the same as that of Example 1, 2-methyl-4,5-dibromo-2H-1,2,3-triazole was replaced with 4.38 g (12.45 mmol) of 2-m-chlorobenzyl-4,5-dibromo-2H-1,2,3-triazole. 3.25 g of 2-m-chlorobenzyl-4-bromo-5-chloro-2H-1,2,3-triazole solid was obtained, the yield was 85%. ¹H NMR (CDCl₃, 400 MHz): δ 7.34-7.30 (m, 3H), 7.22 (dt, J=1.6, 7.2 Hz, 1H), 5.45 (s, 2H); ¹³C NMR (CDCl₃, 400 MHz): δ 137.8, 135.6, 134.9, 130.3, 129.2, 128.5, 126.5, 121.7, 59.4.

EXAMPLE 15

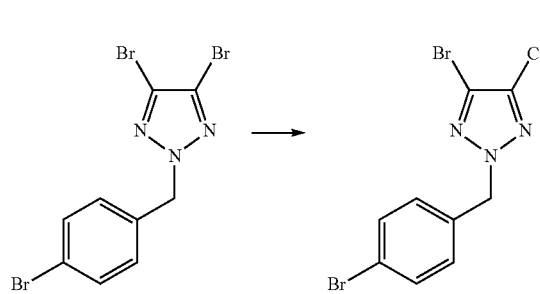 [SMILES: Brc1ccc(Cn2nc(Br)c(Br)n2)cc1 ; Clc1nn(Cc2ccc(Br)cc2)nc1Br]

The operation method was the same as that of Example 1, 2-methyl-4,5-dibromo-2H-1,2,3-triazole was replaced with 4.93 g (12.45 mmol) of 2-p-bromobenzyl-4,5-dibromo-2H-1,2,3-triazole. 3.67 g of 2-p-bromobenzyl-4-bromo-5-chloro-2H-1,2,3-triazole solid was obtained, the yield was 84%. $^1$H NMR (CDCl$_3$, 400 MHz): δ 7.50 (ABq, J=8.4 Hz, 2H), 7.23 (ABq, J=8.4 Hz, 2H), 5.43 (s, 2H); $^{13}$C NMR (CDCl$_3$, 400 MHz): δ 137.7, 132.7, 132.2, 130.1, 123.2, 121.6, 59.5.

EXAMPLE 16

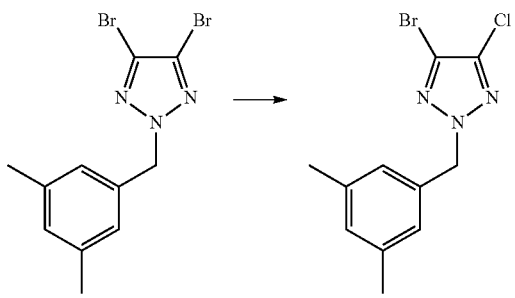 [SMILES: Cc1cc(C)cc(Cn2nc(Br)c(Br)n2)c1 ; Cc1cc(C)cc(Cn2nc(Cl)c(Br)n2)c1]

The operation method was the same as that of Example 1, 2-methyl-4,5-dibromo-2H-1,2,3-triazole was replaced with 4.30 g (12.45 mmol) of 2-(3,5-dimethylbenzyl)-4,5-dibromo-2H-1,2,3-triazole. 3.29 g of 2-(3,5-dimethylbenzyl)-4-bromo-5-chloro-2H-1,2,3-triazole solid was obtained, the yield was 88%. $^1$H NMR (CDCl$_3$, 400 MHz): δ 6.98 (s, 1H), 6.97 (s, 2H), 5.40 (s, 2H), 2.31 (s, 6H); $^{13}$C NMR (CDCl$_3$, 400 MHz): δ 138.7, 137.4, 133.6, 130.6, 126.2, 121.2, 60.3, 21.4.

EXAMPLE 17

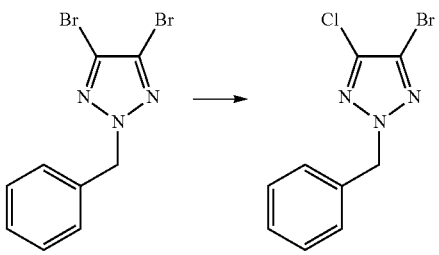 [SMILES: Brc1nn(Cc2ccccc2)nc1Br ; Clc1nn(Cc2ccccc2)nc1Br]

The operation method was the same as that of Example 1, 2-methyl-4,5-dibromo-2H-1,2,3-triazole was replaced with 3.95 g (12.45 mmol) of 2-benzyl-4,5-dibromo-2H-1,2,3-triazole. 3.12 g of 2-benzyl-4-bromo-5-chloro-2H-1,2,3-triazole oily matter was obtained, the yield was 92%. $^1$H NMR (CDCl$_3$, 500 MHz): δ 7.39-7.33 (m, 5H), 5.48 (s, 2H); $^{13}$C NMR (CDCl$_3$, 500 MHz): δ 137.5, 133.9, 129.0, 128.9, 128.4, 121.3, 60.3.

EXAMPLE 18

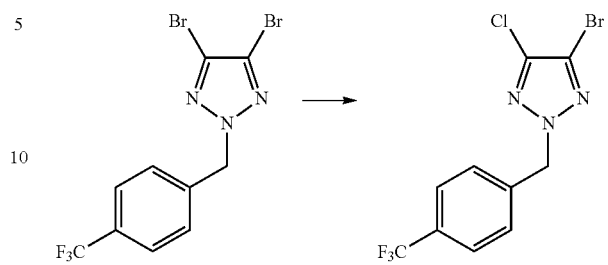

The operation method was the same as that of Example 1, 2-methyl-4,5-dibromo-2H-1,2,3-triazole was replaced with 4.80 g (12.45 mmol) of 2-p-trifluoromethylbenzyl-4,5-dibromo-2H-1,2,3-triazole. 3.18 g of 2-p-trifluoromethylbenzyl-4-bromo-5-chloro-2H-1,2,3-triazole solid was obtained, the yield was 75%. $^1$H NMR (CDCl$_3$, 400 MHz): δ 7.63 (ABq, J=8.0 Hz, 2H), 7.46 (ABq, J=8.0 Hz, 2H), 5.54 (s, 2H).

EXAMPLE 19

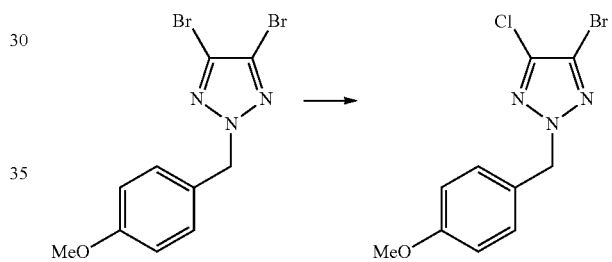

The operation method was the same as that of Example 1, 2-methyl-4,5-dibromo-2H-1,2,3-triazole was replaced with 4.32 g (12.45 mmol) of 2-p-methoxybenzyl-4,5-dibromo-2H-1,2,3-triazole. 3.28 g of 2-p-methoxybenzyl-4-bromo-5-chloro-2H-1,2,3-triazole solid was obtained, the yield was 87%. $^1$H NMR (CDCl$_3$, 400 MHz): δ 7.31 (ABq, J=8.8 Hz, 2H), 6.89 (ABq, J=8.8 Hz, 2H), 5.41 (s, 2H), 3.80 (s, 3H); $^{13}$C NMR (CDCl$_3$, 400 MHz): δ 160.1, 137.3, 130.0, 125.9, 121.1, 114.3, 59.8, 55.3.

EXAMPLE 20

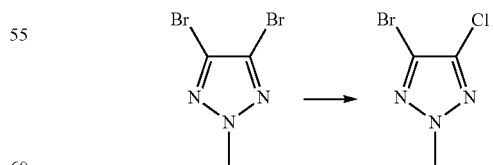

The operation method was the same as that of Example 1, chlorine was replaced with 1.66 g (12.45 mmol) of N-chlorosuccinimide. 1.47 g of 2-methyl-4-bromo-5-chloro-2H-1,2,3-triazole solid was obtained, the yield was 60%. $^1$H NMR (CDCl$_3$, 400 MHz): δ 4.15 (s, 3H); $^{13}$C NMR (CDCl$_3$, 400 MHz): δ 137.0, 120.8, 43.1.

EXAMPLE 21

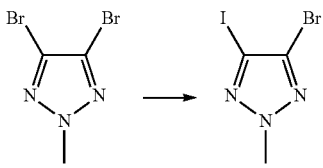

1.20 g (5.0 mmol) of 2-methyl-4,5-dibromo-2H-1,2,3-triazole was dissolved in 10 ml of tetrahydrofuran, cooled to −20~0° C., 2.74 ml (5.18 mmol) of 2.0M isopropylmagnesium tetrahydrofuran solution was added dropwise slowly over 30 minutes. Once the dropwise addition was completed, stirring was continued for 30~60 minutes. 1.26 g (5.0 mmol) of solid iodine was added, continued to react for 30 minutes. Reaction liquid was added by 20 ml of saturated ammonium chloride aqueous solution, extracted using 30 ml of ethyl acetate, dried by anhydrous sodium sulfate, and was concentrated to dry under reduced pressure. The residual solid was added by 10 ml of isopropanol/water (5/1), heated to reflux for 1 hour, cooled to 0~10° C., continued to be stirred for 1 hour, filtered, vacuum dried under a temperature <40° C. 1.16 g of 2-methyl-4-bromo-5-iodo-2H-1,2,3-triazole solid was obtained, and the yield was 81%. $^1$H NMR (CDCl$_3$, 400 MHz): δ 4.20 (s, 3H); $^{13}$C NMR (CDCl$_3$, 400 MHz): δ 130.4, 94.6, 43.0.

EXAMPLE 22

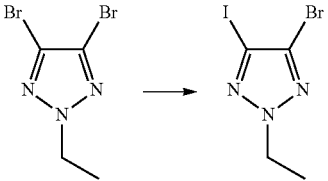

The operation method was the same as that of Example 21, 2-methyl-4,5-dibromo-2H-1,2,3-triazole was replaced with 1.17 g (5 mmol) of 2-ethyl-4,5-dibromo-2H-1,2,3-triazole. 1.28 g of 2-ethyl-4-bromo-5-iodo-2H-1,2,3-triazole solid was obtained, the yield was 85%. $^1$H NMR (CDCl$_3$, 400 MHz): δ 4.46 (q, J=7.2 Hz, 2H), 1.55 (t, J=7.2 Hz, 3H); $^{13}$C NMR (CDCl$_3$, 400 MHz): δ 130.2, 94.3, 51.6, 14.7.

EXAMPLE 23

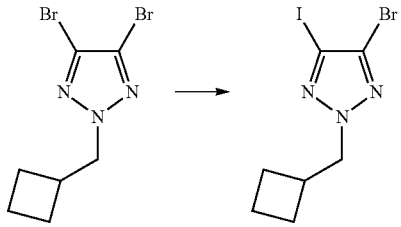 [SMILES: Brc1nn(CC2CCC2)nc1Br ; Brc1nn(CC2CCC2)nc1I]

The operation method was the same as that of Example 21, 2-methyl-4,5-dibromo-2H-1,2,3-triazole was replaced with 1.48 g (5 mmol) of 2-cyclobutylmethyl-4,5-dibromo-2H-1,2,3-triazole. 1.33 g of 2-cyclobutylmethyl-4-bromo-5-iodo-2H-1,2,3-triazole solid was obtained, the yield was 78%. $^1$H NMR (CDCl$_3$, 400 MHz): δ 4.41 (d, J=7.6 Hz, 2H), 2.94-2.86 (m, 1H), 2.11-2.04 (m, 2H), 1.96-1.78 (m, 4H); $^{13}$C NMR (CDCl$_3$, 400 MHz): δ 130.2, 94.3, 61.2, 35.1, 25.6, 18.2.

EXAMPLE 24

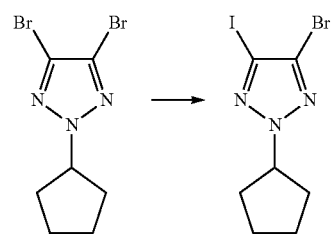 [SMILES: Brc1nn(C2CCCC2)nc1Br ; Brc1nn(C2CCCC2)nc1I]

The operation method was the same as that of Example 21, 2-methyl-4,5-dibromo-2H-1,2,3-triazole was replaced with 1.47 g (5 mmol) of 2-cyclopentyl-4,5-dibromo-2H-1,2,3-triazole. 1.37 g of 2-cyclopentyl-4-bromo-5-iodo-2H-1,2,3-triazole solid was obtained, the yield was 80%. $^1$H NMR (CDCl$_3$, 400 MHz): δ 5.00-4.93 (m, 1H), 2.18-2.12 (m, 4H), 1.93-1.82 (m, 2H), 1.73-1.67 (m, 2H); $^{13}$C NMR (CDCl$_3$, 400 MHz): δ 129.8, 93.9, 67.9, 32.8, 24.3.

EXAMPLE 25

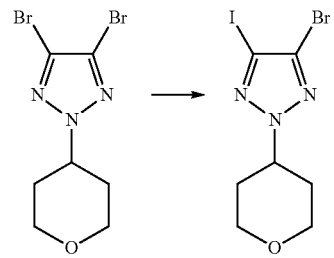

The operation method was the same as that of Example 21, 2-methyl-4,5-dibromo-2H-1,2,3-triazole was replaced with 1.55 g (5 mmol) of 2-(4-tetrahydropyran)-4,5-dibromo-2H-1,2,3-triazole. 1.47 g of 2-(4-tetrahydropyran)-4-bromo-5-iodo-2H-1,2,3-triazole solid was obtained, the yield was 82%. $^1$H NMR (CDCl$_3$, 400 MHz): δ 4.65-4.51 (m, 1H), 4.07 (dt, J=4.0, 11.6 Hz, 2H), 3.52 (dt, J=2.0, 11.6 Hz, 2H), 2.25-2.11 (m, 4H); $^{13}$C NMR (CDCl$_3$, 400 MHz): δ 130.3, 94.6, 66.2, 62.5, 32.2.

EXAMPLE 26

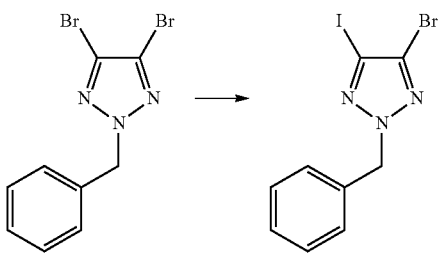

The operation method was the same as that of Example 21, 2-methyl-4,5-dibromo-2H-1,2,3-triazole was replaced with 1.58 g (5 mmol) of 2-benzyl-4,5-dibromo-2H-1,2,3-triazole. 1.45 g of 2-benzyl-4-bromo-5-iodo-2H-1,2,3-triazole solid was obtained, the yield was 80%. ¹H NMR (CDCl₃, 400 MHz): δ 7.37-7.33 (m, 5H), 5.55 (s, 2H); ¹³C NMR (CDCl₃, 400 MHz): δ 134.0, 131.0, 129.0, 128.9, 128.4, 95.2, 60.1.

EXAMPLE 27

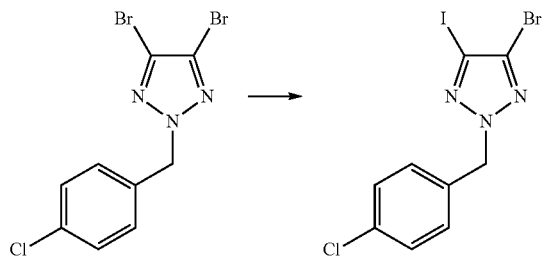

The operation method was the same as that of Example 21, 2-methyl-4,5-dibromo-2H-1,2,3-triazole was replaced with 1.75 g (5 mmol) of 2-p-chlorobenzyl-4,5-dibromo-2H-1,2,3-triazole. 1.59 g of 2-p-chlorobenzyl-4-bromo-5-iodo-2H-1,2,3-triazole solid was obtained, the yield was 80%. ¹H NMR (CDCl₃, 400 MHz): δ 7.33 (ABq, J=3.6 Hz, 2H), 7.30 (ABq, J=3.6 Hz, 2H), 5.51 (s, 2H); ¹³C NMR (CDCl₃, 400 MHz): δ 135.0, 132.4, 131.2, 129.8, 129.2, 95.5, 59.4.

EXAMPLE 28

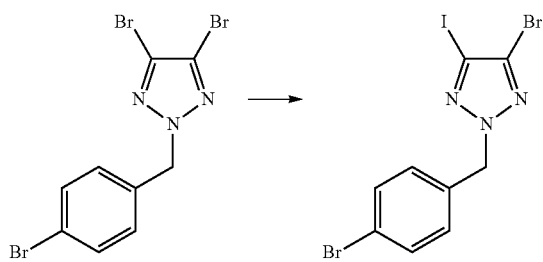 [SMILES: Clc1ccc(Cn2nc(Br)c(Br)n2)cc1 ; Clc1ccc(Cn2nc(Br)c(I)n2)cc1]

The operation method was the same as that of Example 21, 2-methyl-4,5-dibromo-2H-1,2,3-triazole was replaced with 1.98 g (5 mmol) of 2-p-bromobenzyl-4,5-dibromo-2H-1,2,3-triazole. 1.86 g of 2-p-bromobenzyl-4-bromo-5-iodo-2H-1,2,3-triazole solid was obtained, the yield was 84%. ¹H NMR (CDCl₃, 400 MHz): δ 7.49 (ABq, J=8.4 Hz, 2H), 7.22 (ABq, J=8.4 Hz, 2H), 5.49 (s, 2H); ¹³C NMR (CDCl₃, 400 MHz): δ 132.9, 132.2, 131.2, 130.1, 123.2, 95.5, 59.4.

EXAMPLE 29

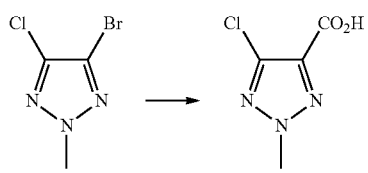

1.96 g (10 mmol) of 2-methyl-4-bromo-5-chloro-1,2,3-triazole was dissolved in 20 ml of tetrahydrofuran, cooled to −20~−10° C., 9.0 ml (11.71 mmol) of 2.0M isopropylmagnesium chloride lithium chloride composite tetrahydrofuran solution was added dropwise slowly over 30 minutes. Once the dropwise addition was completed, stirring was continued for 30~60 minutes. Carbon dioxide was inleted slowly for about 1 minute until reaction liquid was no longer heating up. Reaction liquid was added by 30 ml of 0.5 mole/liter hydrochloric acid solution, extracted using 30 ml of ethyl acetate, dried by anhydrous sodium sulfate, and was concentrated to dry under reduced pressure. The residual solid was added by 20 ml of methyl tertiary butyl ether/n-hexane (1/10), heated to reflux for 1 hour, cooled to 0~10° C., continued to be stirred for 1 hour, filtered, vacuum dried under a temperature <40° C. 1.4 g of 2-methyl-5-chloro-2H-1,2,3-triazole-4-carboxylic acid solid was obtained, and the yield was 85%. ¹H NMR (DMSO-d₆, 400 MHz): δ 4.21 (s, 3H); ¹³C NMR (DMSO-d₆, 400 MHz): δ 160.1, 137.1, 135.2, 42.9.

EXAMPLE 30

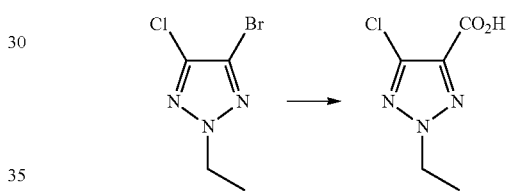

The operation method was the same as that of Example 29, 2-methyl-4-chloro-5-bromo-2H-1,2,3-triazole was replaced with 2.10 g (10 mmol) of 2-ethyl-4-chloro-5-bromo-2H-1,2,3-triazole. 1.54 g of 2-ethyl-5-chloro-2H-1,2,3-triazole-4-carboxylic acid solid was obtained, the yield was 88%. ¹H NMR (CD₃COCD₃, 400 MHz): δ 4.53 (q, J=7.2 Hz, 2H), 1.56 (t, J=7.2 Hz, 3H); ¹³C NMR (CD₃COCD₃, 400 MHz): δ 160.5, 138.8, 135.9, 52.3, 14.6.

EXAMPLE 31

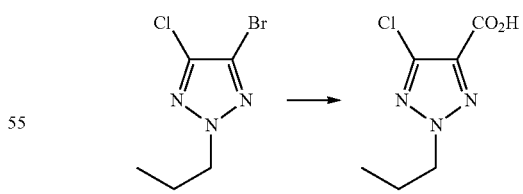

The operation method was the same as that of Example 29, 2-methyl-4-chloro-5-bromo-2H-1,2,3-triazole was replaced with 2.24 g (10 mmol) of 2-n-propyl-4-chloro-5-bromo-2H-1,2,3-triazole. 1.61 g of 2-n-propyl-5-chloro-2H-1,2,3-triazole-4-carboxylic acid solid was obtained, the yield was 85%. ¹H NMR (CD₃COCD₃, 400 MHz): δ 4.53 (q, J=7.2 Hz, 2H), 1.56 (t, J=7.2 Hz, 3H); ¹³C NMR (CD₃COCD₃, 400 MHz): δ 160.5, 138.8, 135.9, 52.3, 14.6.

EXAMPLE 32

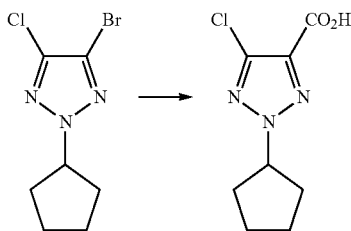 [SMILES: Clc1nn(C2CCCC2)nc1Br ; O=C(O)c1nn(C2CCCC2)nc1Cl]

The operation method was the same as that of Example 29, 2-methyl-4-chloro-5-bromo-2H-1,2,3-triazole was replaced with 2.51 g (10 mmol) of 2-cyclopentyl-4-chloro-5-bromo-2H-1,2,3-triazole. 1.94 g of 2-cyclopentyl-5-chloro-2H-1,2,3-triazole-4-carboxylic acid solid was obtained, the yield was 90%. $^1$H NMR (CD$_3$COCD$_3$, 400 MHz): δ 5.11-5.07 (m, 1H), 2.27-2.14 (m, 4H), 1.91-1.86 (m, 2H), 1.79-1.72 (m, 2H); $^{13}$C NMR (CD$_3$COCD$_3$, 400 MHz) δ 160.5, 138.7, 135.6, 68.6, 33.2, 24.9.

EXAMPLE 33

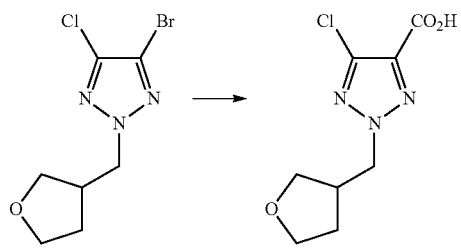 [SMILES: Clc1nn(CC2CCOC2)nc1Br ; O=C(O)c1nn(CC2CCOC2)nc1Cl]

The operation method was the same as that of Example 29, 2-methyl-4-chloro-5-bromo-2H-1,2,3-triazole was replaced with 2.67 g (10 mmol) of 2-(tetrahydrofuran-3-methyl)-4-chloro-5-bromo-2H-1,2,3-triazole. 1.92 g of 2-(tetrahydrofuran-3-methyl)-5-chloro-2H-1,2,3-triazole-4-carboxylic acid solid was obtained, the yield was 83%. $^1$H NMR (CD$_3$COCD$_3$, 500 MHz): δ 4.51 (d, J=7.5, 2H), 3.85 (m, 1H), 3.78 (dd, J=7.0, 9.0 Hz, 1H), 3.69 (q, J=7.0 Hz, 1H), 3.60 (dd, J=5.0, 9.0 Hz, 1H), 2.95-2.88 (m, 1H), 2.11-2.04 (m, 1H), 1.77-1.68 (m, 1H); $^{13}$C NMR (CD$_3$COCD$_3$, 500 MHz) δ 160.4, 139.1, 136.1, 71.0, 67.8, 59.3, 40.1, 30.2.

EXAMPLE 34

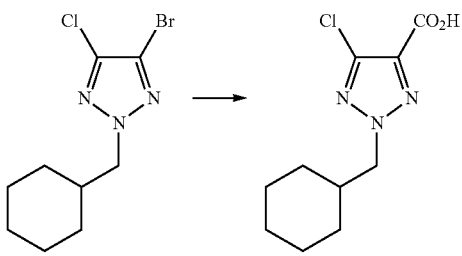 [SMILES: Clc1nn(CC2CCCCC2)nc1Br ; O=C(O)c1nn(CC2CCCCC2)nc1Cl]

The operation method was the same as that of Example 29, 2-methyl-4-chloro-5-bromo-2H-1,2,3-triazole was replaced with 2.78 g (10 mmol) of 2-cyclohexyl methyl-4-chloro-5-bromo-2H-1,2,3-triazole. 2.02 g of 2-cyclohexyl methyl-5-chloro-2H-1,2,3-triazole-4-carboxylic acid solid was obtained, the yield was 83%. $^1$H NMR (CD$_3$COCD$_3$, 400 MHz): δ 4.32 (d, J=7.2 Hz, 2H), 2.07-2.00 (m, 1H), 1.75-1.61 (m, 5H), 1.32-1.18 (m, 3H), 1.12-1.02 (m, 2H); $^{13}$C NMR (CD$_3$COCD$_3$, 400 MHz): δ 160.5, 138.9, 135.9, 62.9, 39.1, 30.8, 26.8, 26.2.

EXAMPLE 35

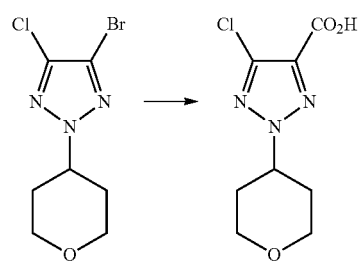 [SMILES: Clc1nn(C2CCOCC2)nc1Br ; O=C(O)c1nn(C2CCOCC2)nc1Cl]

The operation method was the same as that of Example 29, 2-methyl-4-chloro-5-bromo-2H-1,2,3-triazole was replaced with 2.67 g (10 mmol) of 2-(4-tetrahydropyran)-4-chloro-5-bromo-2H-1,2,3-triazole. 2.06 g of 2-(4-tetrahydropyran)-5-chloro-2H-1,2,3-triazole-4-carboxylic acid solid was obtained, the yield was 89%. $^1$H NMR (CD$_3$COCD$_3$, 400 MHz): δ 4.86-4.79 (m, 1H), 4.05 (dt, J=3.6, 11.6 Hz, 2H), 3.59 (dt, J=2.4, 11.6 Hz, 2H), 2.23-2.10 (m, 4H); $^{13}$C NMR (CD$_3$COCD$_3$, 400 MHz): δ 160.5, 138.9, 135.9, 66.5, 63.3, 33.0.

EXAMPLE 36

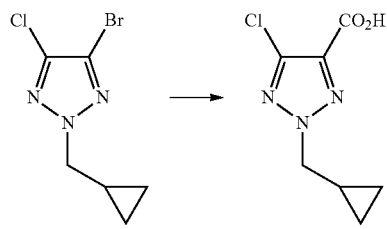 [SMILES: Clc1nn(CC2CC2)nc1Br ; O=C(O)c1nn(CC2CC2)nc1Cl]

The operation method was the same as that of Example 29, 2-methyl-4-chloro-5-bromo-2H-1,2,3-triazole was replaced with 2.36 g (10 mmol) of 2-cyclopropyl methyl-4-chloro-5-bromo-2H-1,2,3-triazole. 1.81 g of 2-cyclopropyl methyl-5-chloro-2H-1,2,3-triazole-4-carboxylic acid solid was obtained, the yield was 90%. $^1$H NMR (CD$_3$COCD$_3$, 400 MHz): δ 4.35 (d, J=7.6 Hz, 2H), 1.47-1.36 (m, 1H), 0.66-0.61 (m, 2H), 0.51-0.47 (m, 2H); $^{13}$C NMR (CD$_3$COCD$_3$, 400 MHz): δ 160.5, 138.9, 136.0, 61.3, 11.4, 4.2.

EXAMPLE 37

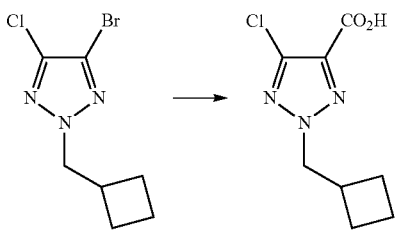 [SMILES: Clc1nn(CC2CCC2)nc1Br ; O=C(O)c1nn(CC2CCC2)nc1Cl]

The operation method was the same as that of Example 29, 2-methyl-4-chloro-5-bromo-2H-1,2,3-triazole was replaced with 2.50 g (10 mmol) of 2-cyclobutyl methyl-4-chloro-5-bromo-2H-1,2,3-triazole. 1.77 g of 2-cyclobutyl methyl-5-chloro-2H-1,2,3-triazole-4-carboxylic acid solid was obtained, the yield was 82%. $^1$H NMR (CD$_3$COCD$_3$, 400 MHz): δ 4.50 (d, J=7.2 Hz, 2H), 2.99-2.91 (m, 1H), 2.11-2.05 (m, 2H), 1.95-1.89 (m, 4H); $^{13}$C NMR (CD$_3$COCD$_3$, 400 MHz) δ 160.5, 138.9, 136.0, 61.6, 35.8, 26.1, 18.6.

EXAMPLE 38

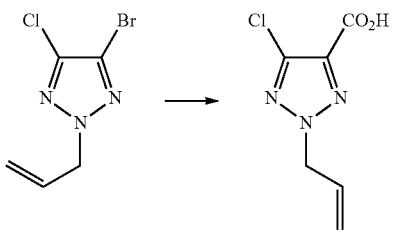

The operation method was the same as that of Example 29, 2-methyl-4-chloro-5-bromo-2H-1,2,3-triazole was replaced with 2.22 g (10 mmol) of 2-allyl-4-chloro-5-bromo-2H-1,2,3-triazole. 1.18 g of 2-allyl-5-chloro-2H-1,2,3-triazole-4-carboxylic acid solid was obtained, the yield was 63%. $^1$H NMR (CDCl$_3$, 400 MHz): δ 6.18-6.08 (m, 1H), 5.37 (dd, J=1.2, 6.4 Hz, 1H), 5.34 (s, 1H), 5.12 (dt, J=1.2, 6.4 Hz, 2H); $^{13}$C NMR (CDCl$_3$, 400 MHz) δ 160.4, 139.2, 136.3, 131.9, 120.4, 59.3.

EXAMPLE 39

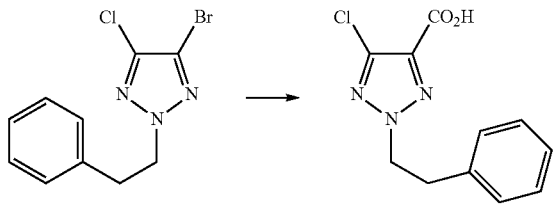 [SMILES: Clc1nn(CCc2ccccc2)nc1Br ; O=C(O)c1nn(CCc2ccccc2)nc1Cl]

The operation method was the same as that of Example 29, 2-methyl-4-chloro-5-bromo-2H-1,2,3-triazole was replaced with 2.87 g (10 mmol) of 2-phenethyl-4-chloro-5-bromo-2H-1,2,3-triazole. 2.16 g of 2-phenethyl-5-chloro-2H-1,2,3-triazole-4-carboxylic acid solid was obtained, the yield was 86%. $^1$H NMR (CDCl$_3$, 400 MHz): δ 7.31-7.20 (m, 5H), 4.73 (t, J=7.2 Hz, 2H), 3.32 (t, J=7.2 Hz, 2H); $^{13}$C NMR (CDCl$_3$, 400 MHz): δ 160.4, 138.9, 138.2, 136.0, 129.6, 129.4, 127.7, 58.2, 35.9.

EXAMPLE 40

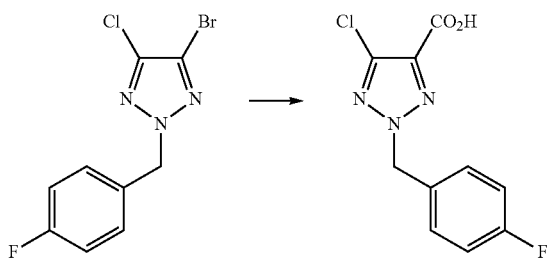 [SMILES: Fc1ccc(Cn2nc(Cl)c(Br)n2)cc1 ; O=C(O)c1nn(Cc2ccc(F)cc2)nc1Cl]

The operation method was the same as that of Example 29, 2-methyl-4-chloro-5-bromo-2H-1,2,3-triazole was replaced with 2.90 g (10 mmol) of 2-p-fluorobenzyl-4-chloro-5-bromo-2H-1,2,3-triazole. 1.97 g of 2-p-fluorobenzyl-5-chloro-2H-1,2,3-triazole-4-carboxylic acid solid was obtained, the yield was 77%. $^1$H NMR (CD$_3$COCD$_3$, 400 MHz): δ 7.51 (dd, J=5.6, 8.4 Hz, 2H), 7.18 (dd, J=8.4, 8.8 Hz, 2H), 5.69 (s, 2H); $^{13}$C NMR (CD$_3$COCD$_3$, 400 MHz): δ 163.8 (d, J=244.0 Hz), 160.3, 139.4, 136.6, 131.7 (d, J=9.0 Hz), 131.5 (d, J=3.0 Hz), 116.5 (d, J=21.0 Hz), 59.8.

EXAMPLE 41

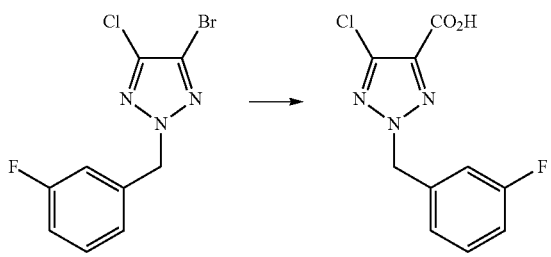 [SMILES: Fc1cccc(Cn2nc(Cl)c(Br)n2)c1 ; O=C(O)c1nn(Cc2cccc(F)c2)nc1Cl]

The operation method was the same as that of Example 29, 2-methyl-4-chloro-5-bromo-2H-1,2,3-triazole was replaced with 2.90 g (10 mmol) of 2-m-fluorobenzyl-4-chloro-5-bromo-2H-1,2,3-triazole. 2.07 g of 2-m-fluorobenzyl-5-chloro-2H-1,2,3-triazole-4-carboxylic acid solid was obtained, the yield was 81%. $^1$H NMR (CD$_3$COCD$_3$, 400 MHz): δ 7.46-7.42 (m, 1H), 7.26 (d, J=7.6 Hz, 1H), 7.23 (dd, J=2.0, 9.6 Hz, 1H), 7.15 (dt, J=2.0, 8.8 Hz, 1H), 5.76 (s, 2H); $^{13}$C NMR (CD$_3$COCD$_3$, 400 MHz): δ 163.6 (d, J=244.0 Hz), 160.4, 139.6, 137.8 (d, J=7.0 Hz), 136.7, 131.7 (d, J=8.0 Hz), 125.2 (d, J=3.0 Hz), 116.4 (d, J=21.0 Hz), 116.2 (d, J=23.0 Hz), 59.9 (d, J=2.0 Hz).

EXAMPLE 42

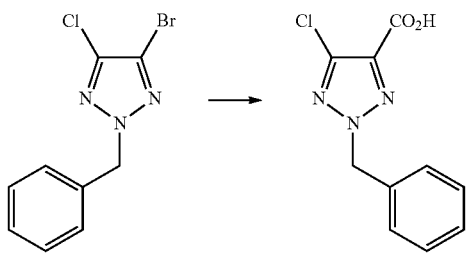 [SMILES: Clc1nn(Cc2ccccc2)nc1Br ; O=C(O)c1nn(Cc2ccccc2)nc1Cl]

The operation method was the same as that of Example 29, 2-methyl-4-chloro-5-bromo-2H-1,2,3-triazole was replaced with 2.72 g (10 mmol) of 2-benzyl-4-chloro-5-bromo-2H-1,2,3-triazole. 1.90 g of 2-benzyl-5-chloro-2H-1,2,3-triazole-4-carboxylic acid solid was obtained, the yield was 80%. $^1$H NMR (CD$_3$COCD$_3$, 400 MHz): δ 7.44-7.35 (m, 5H), 5.69 (s, 2H); $^{13}$C NMR (CD$_3$COCD$_3$, 400 MHz): δ 160.4, 139.4, 136.5, 135.4, 129.7, 129.5, 129.3, 60.6.

EXAMPLE 43

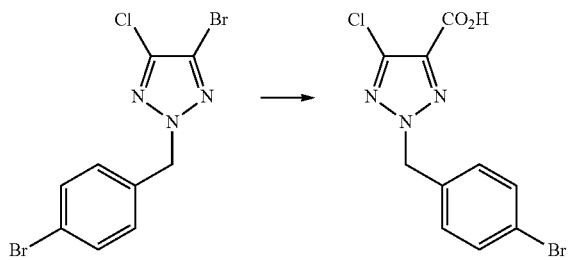 [SMILES: Clc1nn(Cc2ccc(Br)cc2)nc1Br ; O=C(O)c1nn(Cc2ccc(Br)cc2)nc1Cl]

The operation method was the same as that of Example 29, 2-methyl-4-chloro-5-bromo-2H-1,2,3-triazole was replaced with 3.51 g (10 mmol) of 2-p-bromobenzyl-4-chloro-5-bromo-2H-1,2,3-triazole. 2.85 g of 2-p-bromobenzyl-5-chloro-2H-1,2,3-triazole-4-carboxylic acid solid was obtained, the yield was 90%. $^1$H NMR (CD$_3$COCD$_3$, 400 MHz): δ 7.60 (ABq, J=8.4 Hz, 2H), 7.40 (ABq, J=8.4 Hz, 2H), 5.70 (s, 2H); $^{13}$C NMR (CD$_3$COCD$_3$, 400 MHz) δ 160.3, 139.5, 136.7, 134.7, 132.8, 131.5, 123.2, 59.8.

EXAMPLE 44

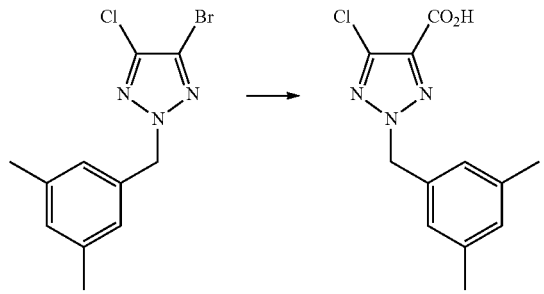 [SMILES: Cc1cc(C)cc(Cn2nc(Cl)c(Br)n2)c1 ; Cc1cc(C)cc(Cn2nc(Cl)c(C(=O)O)n2)c1]

The operation method was the same as that of Example 29, 2-methyl-4-chloro-5-bromo-2H-1,2,3-triazole was replaced with 3.00 g (10 mmol) of 2-(3,5-dimethylbenzyl)-4-chloro-5-bromo-2H-1,2,3-triazole. 2.28 g of 2-(3,5-dimethylbenzyl)-5-chloro-2H-1,2,3-triazole-4-carboxylic acid solid was obtained, the yield was 86%. $^1$H NMR (CD$_3$COCD$_3$, 400 MHz): δ 7.02 (s, 2H), 7.00 (s, 1H), 5.58 (s, 2H), 2.28 (s, 3H), 2.27 (s, 3H); $^{13}$C NMR (CD$_3$COCD$_3$, 400 MHz): δ 160.4, 139.3, 139.2, 136.4, 135.2, 131.0, 127.0, 60.7, 21.2.

EXAMPLE 45

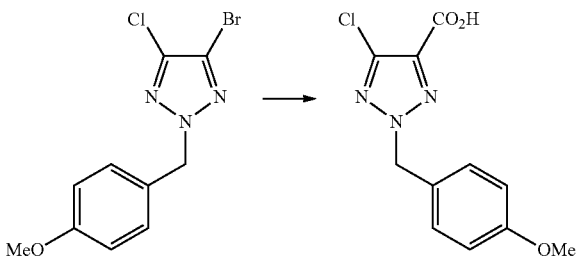 [SMILES: COc1ccc(Cn2nc(Cl)c(Br)n2)cc1 ; COc1ccc(Cn2nc(Cl)c(C(=O)O)n2)cc1]

The operation method was the same as that of Example 29, 2-methyl-4-chloro-5-bromo-2H-1,2,3-triazole was replaced with 3.02 g (10 mmol) of 2-p-methoxybenzyl-4-chloro-5-bromo-2H-1,2,3-triazole. 2.52 g of 2-p-methoxybenzyl-5-chloro-2H-1,2,3-triazole-4-carboxylic acid solid was obtained, the yield was 94%. $^1$H NMR (CD$_3$COCD$_3$, 400 MHz): δ 7.39 (ABq, J=8.8 Hz, 2H), 6.94 (ABq, J=8.8 Hz, 2H), 5.60 (s, 2H), 3.79 (s, 3H); $^{13}$C NMR (CD$_3$COCD$_3$, 400 MHz): δ 161.1, 160.4, 139.3, 136.3, 131.0, 127.2, 115.0, 60.2, 55.6.

Although the present invention has been disclosed as above by better embodiments, it is not used to define the present invention. Slight modifications and improvements can be made by any person skilled in the art without departing from the spirit and scope of the present invention. Accordingly, the scope of protection of the present invention is defined by the follwing claims.

The invention claimed is:
1. A preparation method of the 2-substituted-2H-1,2,3-triazole derivative having the following structure:

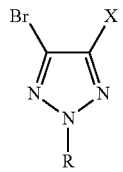

wherein R represents alkyl, aryl, aralkyl, cycloalkyl, cycloalkyl alkyl, heteroaryl, heteroaryl alkyl, or heterocycloalkyl; X represents chlorine or iodine, the method comprising the following steps: dissolving the compound shown in the following formula III in mass to volume ratio of 1:2 to 20 of diethyl ether, tetrahydrofuran or 1,4-dioxane or methyltetrahydrofuran, cooling to −78 to 0° C., adding isopropylmagnesium chloride or isopropylmagnesium chloride-lithium chloride composite, stirring for 0.5 to 2 hours, inleting chlorine or adding N-chlorosuccinimide, 1,3-dichloro-5,5-dimethylhydantoin, or adding iodine, stirring for 5 to 30 minutes, heating up to room temperature, extracting by using organic solvent after quenching by using saturated ammonium chloride aqueous solution, drying via anhydrous sodium sulfate or anhydrous magnesium sulfate, concentrating to dry under reduced pressure, recrystallizing the obtained concentrate to obtain the 2-substituted-2H-1,2,3-triazole derivative;

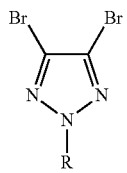

wherein R represents alkyl, aryl, aralkyl, cycloalkyl, cycloalkyl alkyl, heteroaryl, heteroaryl alkyl, or heterocycloalkyl.

2. The preparation method of the 2-substituted-2H-1,2,3-triazole derivative of claim 1, wherein the molar ratio of the compound shown in formula III to isopropylmagnesium chloride or isopropylmagnesium chloride-lithium chloride composite is 1:0 to 1.5, the molar ratio of the compound shown in formula III to chlorine or N-chlorosuccinimide, 1,3-dichloro-5,5-dimethylhydantoin, iodine is 1:1 to 10, the organic solvent is one of or a mixture of two or more than two, in arbitrary proportion, of fatty acids esters or ethers selected from the group consisting of ethyl formate, propyl formate, butyl formate, methyl acetate, ethyl acetate, propyl acetate, butyl acetate, isopropyl acetate, isobutyl acetate, amyl acetate, isoamyl acetate, methyl propionate, ethyl propionate, propyl propionate, butyl propionate and amyl propionate, diethyl ether, propyl ether, isopropyl ether, and methyl tertiary butyl ether.

3. A preparation method of the 2-substituted-2H-1,2,3-triazole derivative, having the following structure:

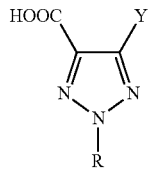

wherein R represents alkyl, aryl, aralkyl, cycloalkyl, cycloalkyl alkyl, heteroaryl, heteroaryl alkyl, or heterocycloalkyl; Y represents chlorine, the method comprising the following steps: dissolving the compound shown in the following formula III in mass to volume ratio of 1:2 to 20 of diethyl ether, tetrahydrofuran or 1,4-dioxane or methyltetrahydrofuran,

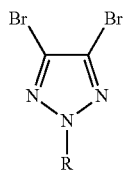

cooling to −78 to 0° C., adding isopropylmagnesium chloride or isopropylmagnesium chloride-lithium chloride composite, stirring for 0.5 to 2 hours, inleting chlorine or adding N-chlorosuccinimide, 1,3-dichloro-5,5-dimethylhydantoin, stirring for about 5 to 30 minutes, heating up to room temperature, extracting by using organic solvent after quenching by using saturated ammonium chloride aqueous solution, drying via anhydrous sodium sulfate or anhydrous magnesium sulfate, concentrating to dry under reduced pressure, recrystallizing the obtained concentrate to obtain 2-substituted-4-bromo-5-chloro-1H-1,2,3-triazole of formula IV

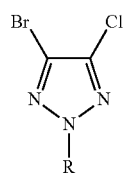

wherein R represents alkyl, aryl, aralkyl, cycloalkyl, cycloalkyl alkyl, heteroaryl, heteroaryl alkyl, or heterocycloalkyl; dissolving the compound shown in formula IV in mass to volume ratio 1:2 to 20 of diethyl ether, tetrahydrofuran, methyltetrahydrofuran or 1,4-dioxane, cooling to −20 to 30° C., adding isopropylmagnesium chloride-lithium chloride composite, stirring for 0.5 to 5 hours, cooling to −50 to 20° C., inleting carbon dioxide gas for about 10 to 30 minutes, heating up to room temperature, extracting by using organic solvent after adjusting pH =1 to 5 by using hydrochloric acid, drying via anhydrous sodium sulfate or anhydrous magnesium sulfate, concentrating to dry under reduced pressure, recrystallizing the obtained concentrate to obtain the 2-substituted-2H-1,2,3-triazole derivative.

4. The preparation method of the 2,4-disubstituted-2H-1,2,3-triazole derivative of claim 3, wherein the molar ratio of the compound of formula III to isopropylmagnesium chloride or isopropylmagnesium chloride-lithium chloride composite is 1:0 to 1.5, the molar ratio of the compound of formula III to carbon dioxide is 1:1 to 10, the organic solvent is one of or a mixture of two or more than two, in arbitrary proportion, of fatty acids esters or ethers selected from the group consisting of ethyl formate, propyl formate, butyl formate, methyl acetate, ethyl acetate, propyl acetate, butyl acetate, isopropyl acetate, isobutyl acetate, amyl acetate, isoamyl acetate, methyl propionate, ethyl propionate, propyl propionate, butyl propionate and amyl propionate, diethyl ether, propyl ether, isopropyl ether, and methyl tertiary butyl ether.

5. The preparation method of 2-substituted-2H-1,2,3-triazole derivative of claim 1, wherein, the recrystallizing includes the following steps: adding the concentrate in solvent according to mass to volume ratio of 1:1 to 100 , stirring for 0.5 to 24 hours at −20 to 50° C., filtering, vacuum drying, obtaining a pure product; wherein the solvent is one of or a mixture of two or more than two, in arbitrary proportion, of water, alcohols, fatty acids esters, ketones, ethers and hydrocarbons selected from the group consisting of methyl alcohol, ethyl alcohol, n-propyl alcohol, isopropanol, n-butyl alcohol, tert-butanol, ethyl formate, propyl formate, butyl formate, methyl acetate, ethyl acetate, propyl acetate, butyl acetate, isopropyl acetate, isobutyl acetate, amyl acetate, isoamyl acetate, methyl propionate, ethyl propionate, propyl propionate, butyl propionate and amyl propionate, acetone, 2-butanone, cyclopentanone and cyclohexanone, diethyl ether, propyl ether, isopropyl ether, methyl tertiary butyl ether and tetrahydrofuran, 1,4-dioxane, petroleum ether, n-hexane, cyclohexane, methylcyclohexane and n-heptane.

6. The preparation method of 2-substituted-2H-1,2,3-triazole derivative of claim 3, wherein, each of the step of recrystallizing the obtained concentrate to obtain 2-substituted-4-bromo-5-chloro-1H-1,2,3-triazole of formula IV and the step of recrystallizing the obtained concentrate to obtain the 2-substituted-2H-1,2,3-triazole derivative includes the following steps: adding the concentrate in solvent according to mass to volume ratio of 1:1 to 100, stirring for 0.5 to 24 hours at −20 to 50° C., filtering, vacuum drying, obtaining a pure product; wherein the solvent is one of or a mixture of two or more than two, in arbitrary proportion, of water, alcohols, fatty acids esters, ketones, ethers and hydrocarbons, selected from the group consisting of methyl alcohol, ethyl alcohol, n-propyl alcohol, isopropanol, n-butyl alcohol, tert-butanol, ethyl formate, propyl formate, butyl formate, methyl acetate, ethyl acetate, propyl acetate, butyl acetate, isopropyl acetate, isobutyl acetate, amyl acetate, isoamyl acetate, methyl propionate, ethyl propionate, propyl propionate, butyl propionate and amyl propionate, acetone, 2-butanone, cyclopentanone and cyclohexanone, diethyl ether, propyl ether, isopropyl ether, methyl tertiary butyl ether and tetrahydrofuran, 1,4-dioxane, petroleum ether, n-hexane, cyclohexane, methylcyclohexane and n-heptane.

\* \* \* \* \*